United States Patent [19]

Kulesz-Martin

[11] Patent Number: 5,726,024
[45] Date of Patent: Mar. 10, 1998

[54] P53AS PROTEIN AND ANTIBODY THEREFOR

[75] Inventor: Molly F. Kulesz-Martin, Buffalo, N.Y.

[73] Assignee: Health Research, Inc., Buffalo, N.Y.

[21] Appl. No.: 644,291

[22] Filed: May 10, 1996

Related U.S. Application Data

[63] Continuation-in-part of Ser. No. 259,612, Jun. 14, 1994, which is a continuation-in-part of Ser. No. 195,952, Feb. 11, 1994, abandoned, which is a continuation-in-part of Ser. No. 100,496, Aug. 2, 1993.

[51] Int. Cl.$^6$ ............... G01N 33/53; G01N 33/577; C07K 16/18; C07K 16/30
[52] U.S. Cl. ............... 435/7.1; 435/7.23; 530/387.7; 530/388.8; 530/388.85; 530/389.7
[58] Field of Search ............... 435/7.1, 7.23; 530/387.7, 388.8, 388.85, 389.7

[56] References Cited

U.S. PATENT DOCUMENTS

4,786,718  11/1988  Weinberg et al.

FOREIGN PATENT DOCUMENTS

0 529 160  3/1993  European Pat. Off.
92/13970  8/1992  WIPO

OTHER PUBLICATIONS

Antibodies—Anti-Oncogenes—p53 and Heat Shock Proteins, Oncogene Science.
Arai, N. et al., (1986) Immunologically Distinct p53 Molecules Generated by Alternative Splicing, Mol. and Cellular Biology, pp. 3232–3239.
Barak, Y. et al., (1993) mdm2 Expression is Induced by Wild Type p53 Activity, The EMBO Journal, vol. 12, No. 2, pp. 461–468.
Bargonetti, J. et al., (1991) Wild–Type but not Mutant p53 Immunopurified Proteins Bind to Sequences Adjacent to the SV40 Origin of Replication, Cell, vol. 65, pp. 1083–1091.
Bargonetti, J. et al. (1993) A Proteolytic Fragment From the Central Region of p53 Has Marked Sequence–Specific DNA–Binding Activity When Generated from Wild–Type but not from Oncogenic Mutant p53 Protein, Genes & Development, 7, pp. 2565–2574.
Bischoff, J. et al., (1992) Human p53 Inhibits Growth in Schizosaccharomyces pombe, Molecular and Cellular Biology, vol. 12, No. 4, pp. 1405–1411.
El–Deiry, W. et al., (1993) WAF12, A Potential Mediator of p53 Tumor Suppression, Cell, vol. 75, pp. 817–825.
El–Deiry, W. et al. (1992) Definition of a Consensus Binding Site for p53, Nature Genetics, vol. 1, pp. 45–49.
Eliyahu et al., (1988) Meth A Fibrosarcoma Cells Express Two Transforming Mutant p53 Species, Oncogene, 3, pp. 313–321.
Farmer, G. et al., (1992) Wild–type p53 Activates Transcription in vitro, Nature, vol. 358, pp. 83–86.
Finlay, C. et al., (1993) The mdm–2 Oncogene Can Overcome Wild–Type 53 Suppression of Transformed Cell Growth, Mol. & Cell. Biol., pp. 301–306.
Friedman, P. et al., (1993) The p53 Proteins is an Unusually Shaped Tetramer that Binds Directly to DNA, Proc. Natl. Acad. Sci. USA, vol. 90, pp. 3319–3323.
Funk, W. et al., (1992) A Transcriptionally Active DNA–Binding Site for Human p53 Protein Complexes, Mol. and Cell. Biol., pp. 2866–2871.
Gannon J. et al., (1990) Activating Mutations in p53 Produce a Common Conformational Effect, A Monoclonal Antibody Specific for the Mutant Form, The EMBO Journal, vol. 9, No. 5, pp. 1595–1602.
Gu, Y. et al., (1993) Inhibition of CDK2 Activity in vivo by an Associated 20K Regulatory Subunit, Nature, vol. 366, pp. 707–710.
Gupta R. K. et al., (1993) Mutation of p53 in Primary Biopsy Material and Cell Lines From Hodgkin Disease, Proc. Natl. Acad. Sci., vol. 90, pp. 2817–2821.
Hainaut, P. et al., (1992) Interaction of Heat–Shock Protein 70 with p53 Translated in vitro: Evidence for Interaction with Dimeric p53 and for a Role in the Regulation of p53 Conformation, The EMBO Journal, vol. 11, No. 10, pp. 3513–3520.
Halazonetis, T. et al., (1993) Wild–Type p53 Adopts a "Mutant"–Like Conformation When Bound to DNA, The EMBO Journal, vol. 12, No. 3, pp. 1021–1028.
Han, K. et al., (1992) Alternatively Spliced p53 RNA in Transformed and Normal Cells of Different Tissue Types, Nuc. Acid Res. vol. 20, No. 8, pp. 1979–1981.
Harper, J. et al., (1993) The p21 Cdk–Interacting Protein Cip1 is a Potent Inhibitor of G1 Cyclin–Dependent Kinases, Cell, vol. 75, pp. 805–816.
Hupp, T. et al., (1992) Regulation of the Specific DNA Binding Function of p53, Cell, vol. 71, pp. 875–886.

(List continued on next page.)

*Primary Examiner*—Lila Feisee
*Assistant Examiner*—Nancy A. Johnson
*Attorney, Agent, or Firm*—Michael L. Dunn

[57] ABSTRACT

The invention comprises plasmids and viral vectors containing an animal p53as cDNA sequence. A portion of the p53as sequence may be identified to a position of wild type p53 gene from the same animal. In preferred embodiments, the p53as is mouse or human p53as. A preferred viral vector is baculovirus vector. The invention further includes antibodies both polyclonal and monoclonal, to p53as and to at least a portion of human p53 intron 10 sequence encoding SLR-PFKALVREKGHRPSSHSC (SEQ ID NO: 1) which is related to p53as sequences and plasmids and viral vectors containing such sequences. All of the above find utility in studying p53 and p53as and their relative expressions which is believed important for detection and control of malignant cells and their susceptibility to treatment agents. The antibodies can detect the presence of p53as and related sequences and when injected into cells could cause cell cycle arrest and the plasmids and viral vectors, with appropriate promotors, can cause expression of the p53as and p53 intron 10 sequences which can affect cell growth and perhaps arrest certain malignancies.

5 Claims, 13 Drawing Sheets

OTHER PUBLICATIONS

Juven, T. et al. (1993) Wild Type p53 Can Mediate Sequence- Specific Transactivation of an Internal Promoter Within the mdm2 Gene, Oncogene, 8, pp. 3411–3416.

Kastan, M. et al., (1991) Participation of p53 Protein in the Cellular Response to DNA Damage, Cancer Research, 51, pp. 6304–6311.

Kastan, M. et al., (1992) A Mammalian Cell Cycle Checkpoint Pathway Utilizing p53 and GADD45 is Defective in Ataxia–Telangiectasia, Cell, vol. 71, pp. 587–597.

Kern, S. et al. (1992) Oncogenic Forms of p53 Inhibit p53–Regulated Gene Expression, Science, vol. 256, pp. 827–830.

Kern, S. et al., (1991) Identification of p53 as a Sequence–Specific DNA–Binding Protein, Science, vol. 252, pp. 1708–1711.

Kuerbitz, S. et al., (1992) Wild–Type p53 is a Cell Cycle Checkpoint Determinant Following Irradiation, Proc. Natl. Acad. Sci. USA, vol. 89, pp. 7491–7495.

Kulesz–Martin, M. et al., Endogenous p53 Protein Generated from Wild–Type Alternatively Spliced p53 RNA in Mouse Epidermal Cells, Molecular and Cellular Biology, vol. 14, pp. 1698–1708.

Lane, D. (1992) p53, Guardian of the Genome, Nature, vol. 358, pp. 15–16.

Milner, J. et al., (1991) Cotranslation of Activated Mutant p53 with Wild Type Drives the Wild–Type p53 Protein into the Mutant Conformation, Cell, vol. 65, pp. 765–774.

Momand, J. et al., (1992) The mdm–2 Oncogene Product Forms a Complex with the p53 Protein and Inhibits p53–Mediated Transactivation, Cell, vol. 69, pp. 1237–1245.

Nigro, J. et al., (1992) Human p53 and CDC2Hs Genese Combine to Inhibit the Proliferation of *Saccharomyces cerevisiae*, Molecular and Cellular Biology, pp. 1357–1365.

Oliner, J. et al., (1992) Amplification of a Gene Encoding a p53–Associated Protein in Human Sarcomas, Nature, vol. 358, pp. 80–83.

Pavletich, N. et al. (1993) The DNA–Binding Domain of p53 Contains the Four Conserved Regions and the Major Mutation Hot Spots, Genes & Development, 7, pp. 2556–2564.

Ro, Y.S. et al., (1993) p53 Protein Expression in Benign and Malignant Skin Tumours, British Journal of Dermatology, 128, 237–241.

Scharer, E. et al. (1992) Mammalian p53 Can Function as a Transcription Factor in Yeast, Nucleic Acids Research, vol. 20, No. 7, pp. 1539–1545.

Serrano, J. et al., (1993) A New Regulatory Motif in Cell–Cycle Control Causing Specific Inhibition of Cyclin D/CDK4, Nature, vol. 366, pp. 704–707.

Stenger, J. et al., (1992) Formation of Stable p53 Homotetramers and Multiples of Tetramers, Molecular Carcinogenesis, 5, pp. 102–106.

Stephen, C. et al., (1992) Mutant Conformation of p53, J. Mol. Biol., 225, pp. 577–583.

Vojtesek, B. et al. (1992) An Immunochemical Analysis of the Human Nuclear Phosphoprotein p53, Journal of Immunological Methods, 151, pp. 237–244.

Wade–Evans, A. et al. (1985) Precise Epitope Mapping of the Murine Transformation–Associated Protein, p53, The EMBO Journal, vol. 4, No. 3, pp. 699–706.

Wang, Y. et al. (1993) p53 Domains: Identification and Characterization of Two Autonomous DNA–Binding Regions, Genes & Development, 7, pp. 2575–2586.

Wolf, D. et al., (1985) "Isolation of a Full–Length Mouse cDNA Clone Coding for an Immunologically Distinct p53 Molecule", Molecular and Cellular Biology, vol. 5, #1, pp. 127–132.

Xlong, Y. et al., (1993) p21 is a Universal Inhibitor of Cyclin Kinases, Nature vol. 366, pp. 701–704.

Zambetti, G. et al., (1992) Wild–Type p53 Mediates Positive Regulation of Gene Expression Through a Specific DNA Sequence Element, Genes & Development, 6, pp. 1143–1152.

Zauberman, A. et al. (1993) Sequence–Specific DNA Binding by p53: Identification of Target Sites and Lack of Binding to p53–MDM2 Complexes, The EMBO Journal, vol. 12, No. 7, pp. 2799–2808.

|  | Distribution (%) | |
| --- | --- | --- |
| Stage | p53as(-) | p53as(+) |
| >G2/M | 3.7 | 41.5 |
| G2/M | 45.7 | 35.2 |
| S | 22.7 | 12.1 |
| G0/G1 | 27.7 | 11.2 |
| Total events | 20,000 | 9313 |

| Stage | Distribution (%) | |
|---|---|---|
| | R3 negative cells | p53as(+) |
| >G2/M | 4.1 | 58.0 |
| G2/M | 8.9 | 22.2 |
| S | 12.4 | 12.2 |
| G0/G1 | 74.1 | 7.6 |
| % of total cells | 98.5 | 1.5 |

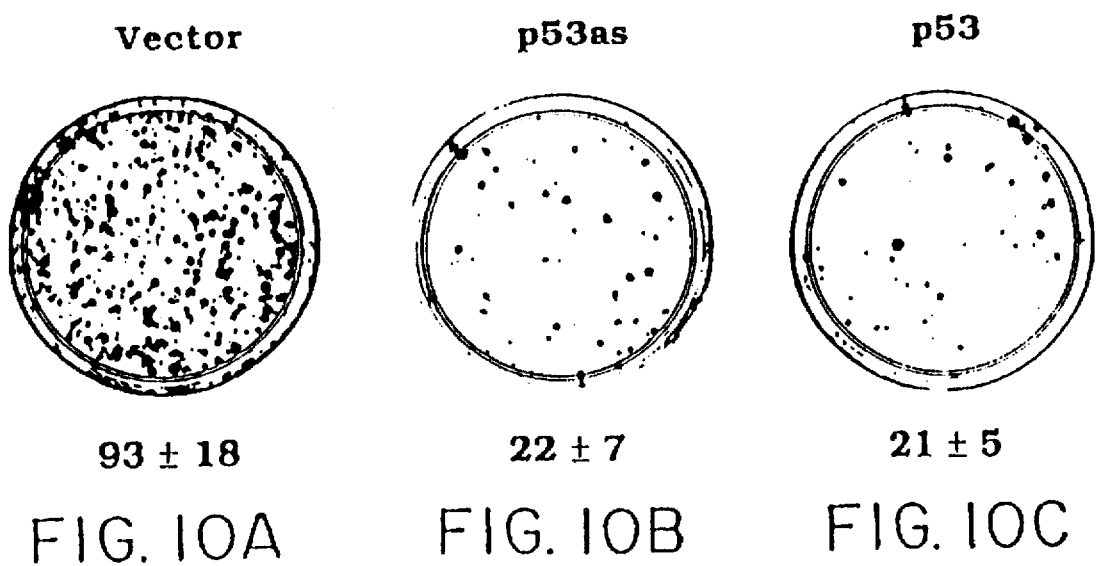

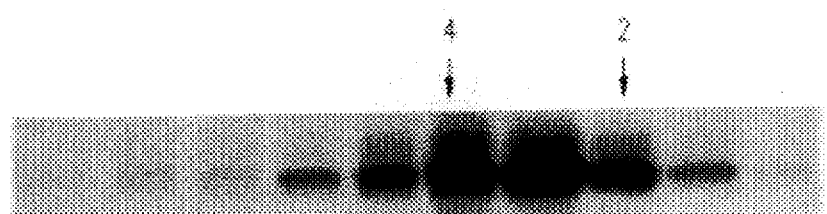
FIG. 11A p53as
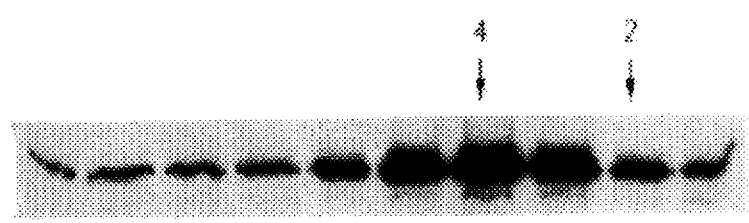
FIG. 11B p53
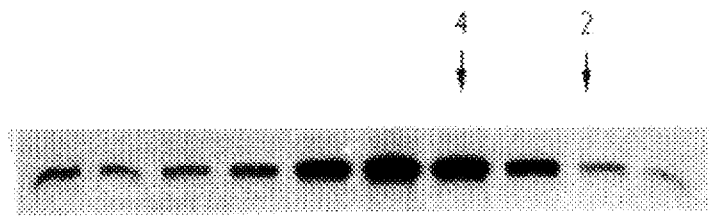
FIG. 11C cotranslated p53 + p53as

P53AS PROTEIN AND ANTIBODY THEREFOR

This is a Continuation-in-part of U.S. patent application Ser. No. 08/259,612 filed Jun. 14, 1994 which is a Continuation-in-part of U.S. patent application Ser. No. 08/195,952 filed Feb. 11, 1994, now abandoned, which is a Continuation-in-part of U.S. application Ser. No. 08/100,496, filed Aug. 2, 1993.

This invention was made with support from National Cancer Institute Grant NIH RO1 CA 31101. The United States Government may have certain rights in the invention.

BACKGROUND OF THE INVENTION

We have demonstrated previously that a wild type alternatively spliced p53 (p53as, for alternative splice) RNA exists in cultured cells and normal tissues at approximately 30% of the major p53 RNA form (Han and Kulesz-Martin, Nucleic Acid Res., 20:1979–81, 1992). The predicted protein encoded by the p53as transcript differs from p53 protein in 17 C-terminal amino acids and is truncated by 9 amino acids due to alternative splicing of intron 10 of the wild type p53 gene. Using antibody to the 17 C-terminal amino acids to detect p53as protein, we have demonstrated the following points. p53as protein is an alternatively spliced product of the wild type p53 gene. First detected in mouse epidermal cells, it is present in non-transformed and malignant cells. Like its major counterpart, p53 protein, it is located in the nucleus. However, while p53 antigen activity is primarily found in cells at the G1 stage of the cell cycle and is thought to play a role in G1 arrest in cells following treatment with DNA damaging agents, p53as is found in cells preferentially distributed in the G2 phase of the cell cycle and in a "tail" of cells with >G2 DNA content. These properties of p53as protein were suggestive of cellular functions distinct from the major p53 protein. The well established ability of the p53 protein to oligomerize and our finding of co-expression of p53as antigen activity with p53 in cells suggested potential for cooperation with p53 in its functions related to cell cycle control. This information is described in detail in the original patent application Ser. No. 08/100,496, filed Aug. 2, 1993 which is incorporated herein by reference.

The presence of the p53as protein in tumor cells and antibodies for its detection has applications in basic research on cell growth and differentiation. Presence of a homologous protein in human cells has applications in the diagnosis, prognosis and design of treatment strategy in human diseases of growth and differentiation such as cancer. The association with G2 suggests a functional role in G2 arrest and potential for gene therapy using the p53as coding sequence.

BRIEF DESCRIPTION OF THE INVENTION

This application provides further support for the utility of p53as expression from plasmids and vectors such as those described in application Ser. No. 08/195,952. Further evidence is presented that p53as protein has "tumor suppressor" activity in mouse and human cells, activates transcription through p53 target sequences of mouse and human cells, and forms tetramers, a DNA binding form observed for the tumor suppressor gene p53as. This Application further claims the use of antibodies to human p53as for diagnosis of human cancers, the use of antibodies to human p53as for determination of prognosis of human cancers and use of antibodies to human p53as for determining a treatment plan for individual patient cancers.

The p53as antibodies having the utilities described may be antibodies to naturally occurring or synthetic. A form of natural p53as is present in normal cells of at least some mammals. p53as is essentially identical to known normal growth controlling protein p53, at least until the final 50 and preferably until the final 30 amino acids of the carboxy terminal end of the protein. "Essentially identical" means at least 80% and preferably at least 90% sequential correspondence with p53. It should be noted that mouse p53 has an 81% identity with mouse p53as at the protein level. Mouse p53as has a highly acidic N terminus, a basic C-terminus and a central region containing uncharged amino acids.

The final 50 amino acids of p53as protein proximate the carboxy terminus of the p53as protein, are at least partly different than the final 50 amino acids of p53 protein. The difference is believed to be at least in part due to different amino acid sequences in the two proteins proximate the carboxy termination of the protein and may also be partly due to a longer or shorter p53as amino acid chain when compared with p53. It is believed that the most common and probable final few amino acids at the carboxy termination of naturally occurring p53as contain the sequences SPNC and SPPC.

p53as has been found to function as a growth regulator in all mammals tested regardless of whether or not p53as has been found to naturally occur in the mammal.

It is to be understood that p53as may be of natural or synthetic form, provided that, at a minimum, terminal amino acids differ in whole or in part from the 50 terminal amino acids of p53 so that the modified products will act the same as active p53 protein and is functionally equivalent to mouse p53as protein.

In general, it can be stated that p53as is functionally the same as p53 except that a p53as lacks the negative regulatory domain for p53 sequence specific DNA binding which is found within the last 50 amino acids at the p53 C terminus. The negative regulatory domain of p53 negates p53 sequence specific binding in certain cellular environments which in turn causes p53 to lose activity. p53as lacks the negative regulatory domain and thus remains active in similar cellular environments. To obtain a p53as the terminal amino acids of p53 are preferably modified, i.e., there is at least some substitution, as opposed to simple truncation.

As described in the parent applications, the invention also comprises plasmids and viral vectors containing a p53as cDNA sequence. A preferred viral vector is baculovirus vector. The invention further includes antibodies both polyclonal and monoclonal, to p53as and to at least a portion of human p53 intron 10 sequence encoding SLR-PFKALVREKGHRPSSHSC which is related to p53as sequences and plasmids and viral vectors containing such sequences.

All of the above find utility in studying p53 and p53as and their relative expressions which is believed important for detection and control of malignant cells and their susceptibility to treatment agents.

The antibodies can detect the presence of p53as and related sequences and when injected into cells could cause cell cycle arrest and the plasmids and viral vectors, with appropriate promotors, can cause expression of the p53as and p53 intron 10 sequences which can affect cell growth and perhaps arrest certain malignancies.

BRIEF DESCRIPTION OF THE DRAWINGS

FIG. 1A shows reactions for p53 and FIG.

1B shows reactions for p53as, respectively. PAb421 is specific for the major p53 form only, and ApAs is specific for p53as protein only. 10 μg of plasmid pBSp53as or pBSp53 was linearized by BamHI and transcribed with 20 Units T3 RNA polymerase. The in vitro translation was performed according to a standard protocol (Promega) by incubating 3 μg RNA with 35 μl of rabbit reticulocyte lysate in the presence of 4 μl (40 μCi) $^{35}$S-methionine for labeling of proteins. For Co-translation of p53as and p53, an equal amount of each RNA was incubated with rabbit reticulocyte lysate (Promega). Immunoprecipitation was performed by incubating 5 μl $^{35}$S-labeled protein with 1 μg PAb421, ApAs or PAb246 at 4° C. overnight. Protein A-Sepharose 4B was then added with gentle mixing at 4° C. for 2 hr. After centrifugation, the pellets were washed three times with Net-gel buffer. The pellets were suspended in 2× sample buffer containing 100 mm DTT and separated by electrophoresis in a 7.5% SDS-polyacrylamide minigel. The gel was enhanced, dried and exposed overnight to Kodak X film. Two lysate reactions are shown, p53 or p53as RNA— see labels at top. Antibodies used to immunoprecipitate protein from each lysate reaction are indicated.

FIG. 2 through FIG. 6 represent electrophoretic mobility shift assays (EMSA) of p53 and p53as proteins translated in vitro using the DNA probe sequence presented in Table 2.

Figures 1A, 1B:
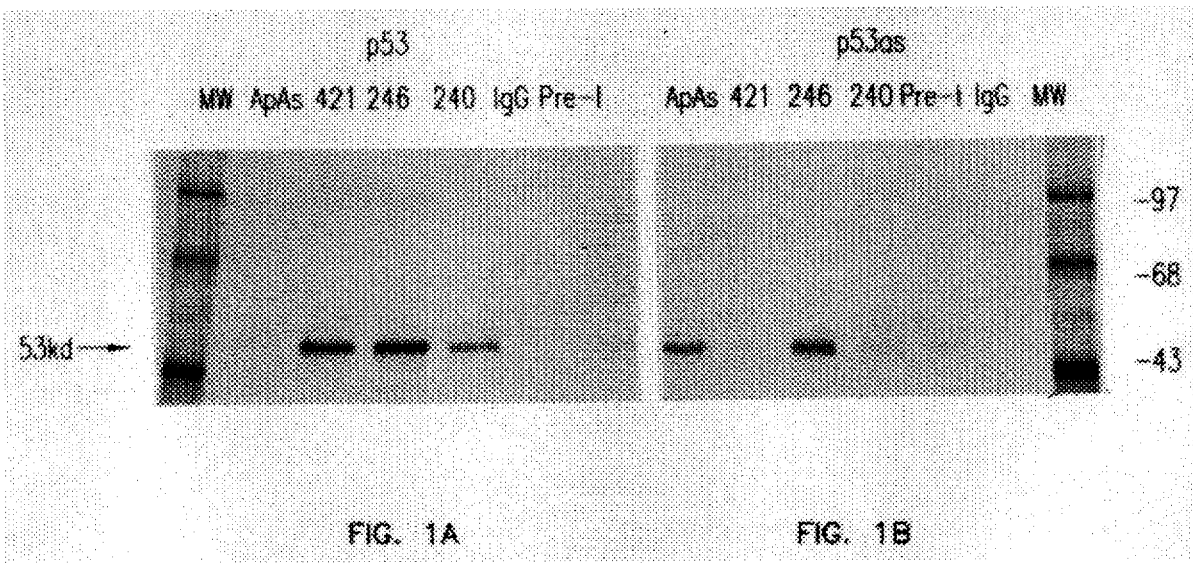
FIGS. 1A and 1B show immunoprecipitation of proteins translated in vitro.
Figure 2:
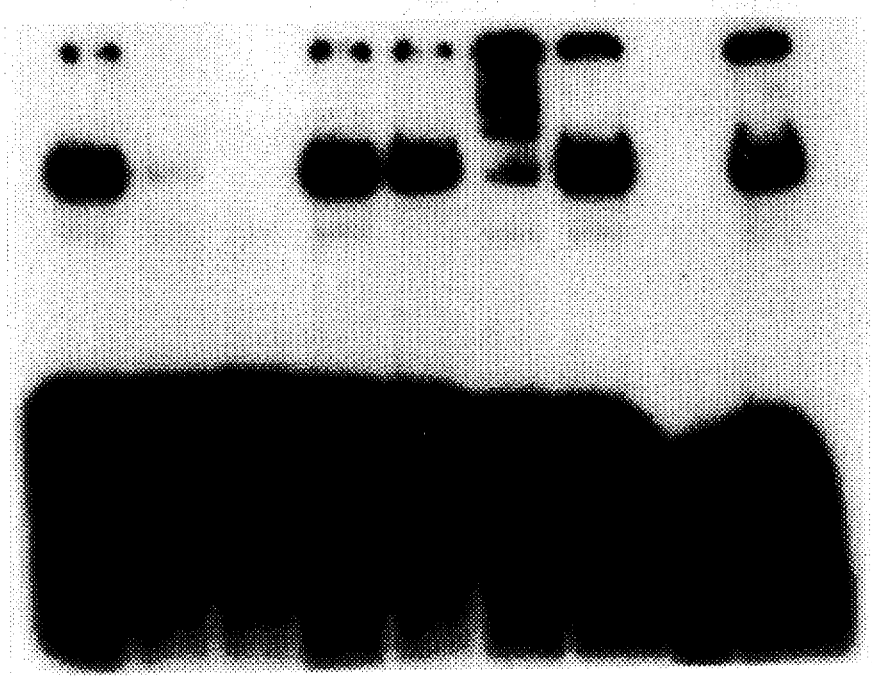

FIG. 2. p53as protein binds specifically and efficiently to DNA. Binding of p53as protein translated in vitro (5 μl of 250 μl reaction) to $^{32}$P-labeled oligonucleotide (ng) in the presence of increasing amount of unlabeled wt p53 binding sequence (wt) or of mutated (mut) sequence (see [1] in Materials and Methods) demonstrates the specificity of p53as protein for the p53 binding motif. 200 ng ApAs antibody to p53as can super-shift the binding complex. 200 ng of pre-immune rabbit serum (Pre) and PAb421 (421) were used as controls.

Figure 3:
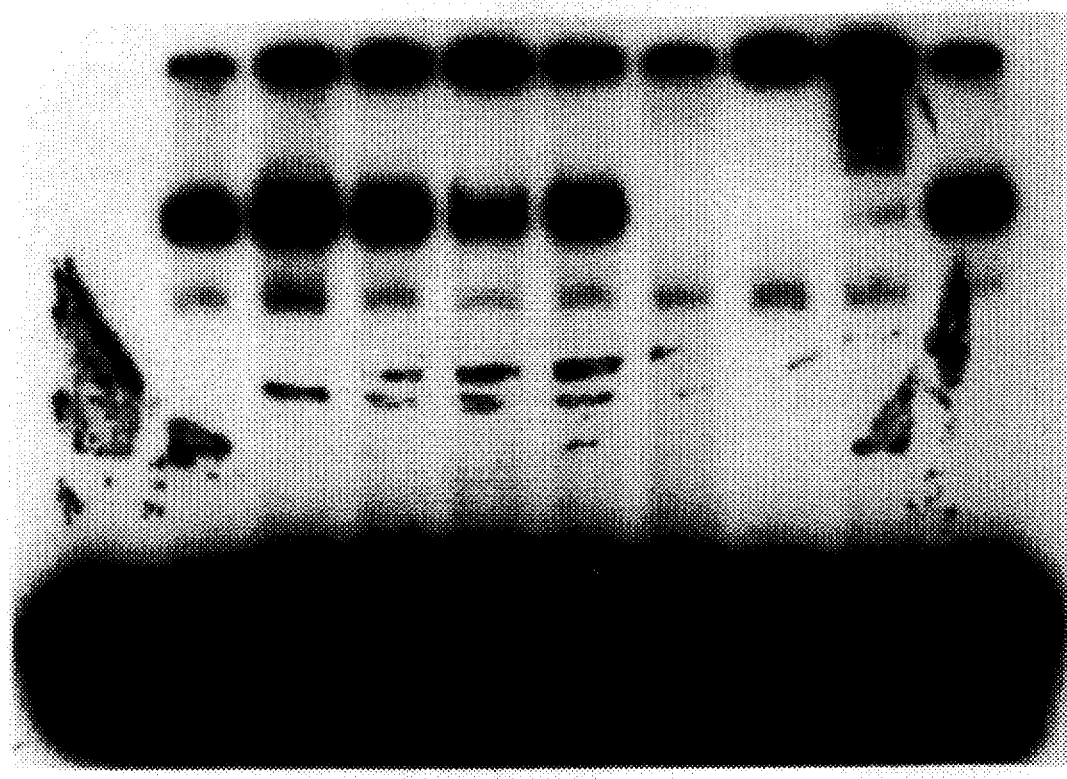

FIG. 3. p53as protein complex with DNA is shifted by anti-p53as (ApAs) and abrogated by anti-p53 antibodies PAb246 (246) and CM5 but not mutant conformation-specific PAb240 (240). p53as protein was translated in vitro in reticulocyte lysates and assayed by EMSA for binding to $^{32}$P-labeled probe in the absence of antibodies (−) or in the presence of PAb421, 200 ng PAb246 and rabbit polyclonal anti-p53 antibody CM5, or 200 ng ApAs. IgG2a (IgG), pre-immune serum (Pre), and non-programmed reticulocyte lysate (Lys) were used as controls.

Figure 4:
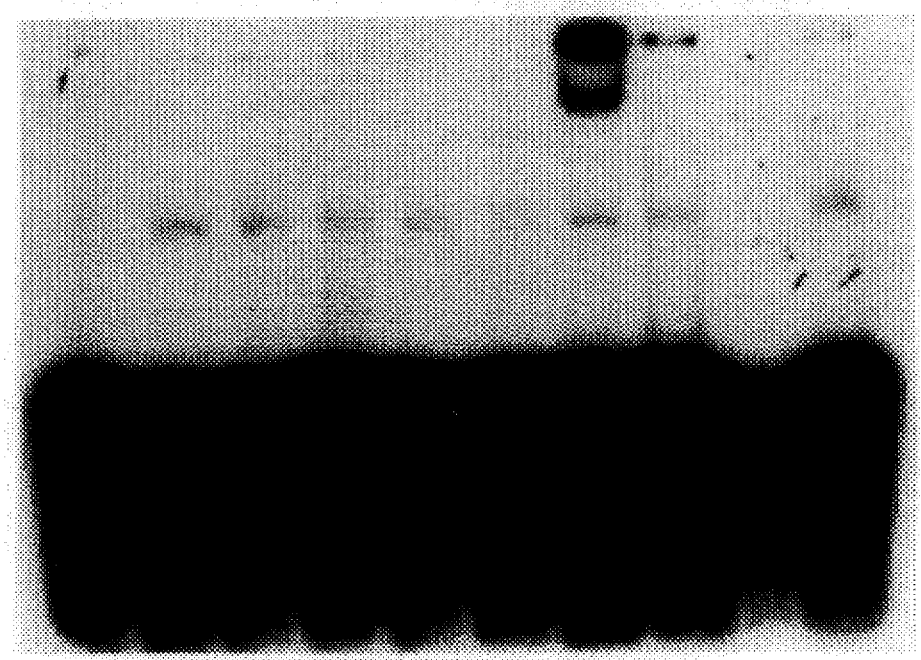

FIG. 4. p53 protein requires activation to bind to DNA. There is no apparent binding to the $^{32}$P-labeled probe by p53 (lanes 2–6, 8–10) as compared to the non-programmed rabbit reticulocyte lysate (lane 1). A binding complex can be detected when 200 ng of PAb421 was included in the reaction (lane 7).

Figure 5:
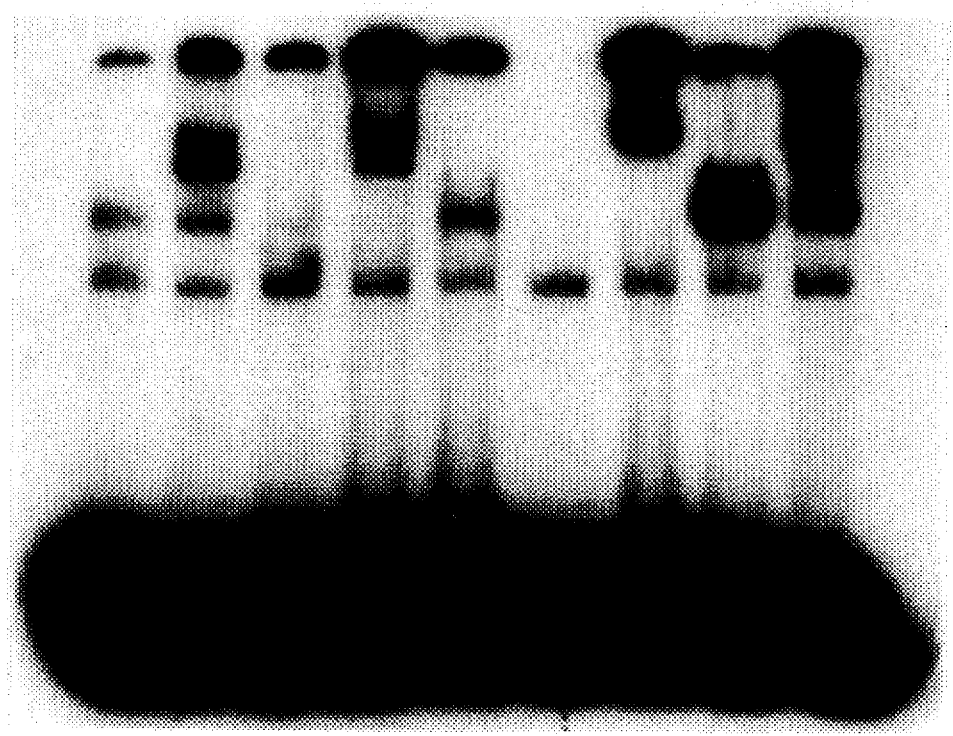

FIG. 5. Interaction of p53as with p53 and its effects on DNA binding activity of p53as. Equal amount of in vitro transcripted p53 and p53as RNAs were co-translated (AP) or translated individually and p53 (P) and p53as (AS) proteins were assayed for their DNA binding activities by EMSA. The co-translated proteins have lower DNA binding activities (lane 1) than p53as alone (lane 8). Two binding complexes can be detected when 200 ng PAb 421 (lane 2) or 200 ng PAb 421 plus ApAs (lane 4) were included in the reactions containing co-translated proteins, while only one binding complex appears as PAb 421 activates p53 DNA binding activity (lane 7). 200 ng ApAs did not cause any apparent supershift for co-translated proteins (lane 3). Two higher molecular weight binding complexes can be seen when ApAs was added to the reaction containing only p53as protein (lane 9).

Figure 6:
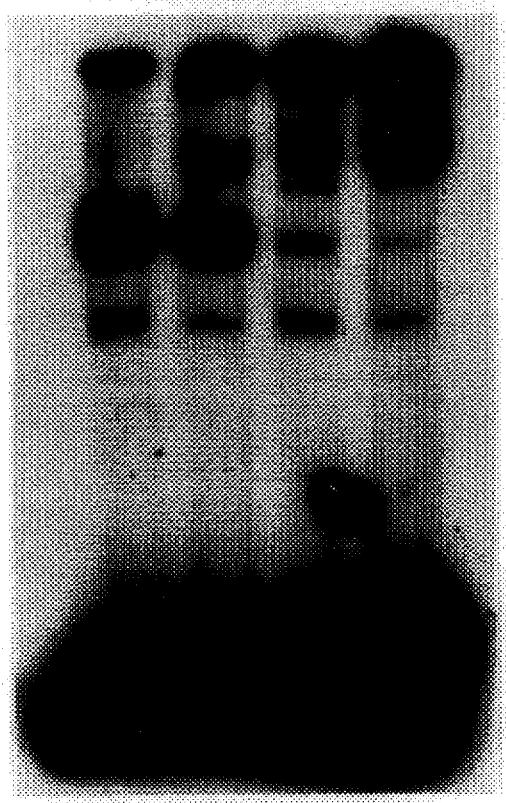

FIG. 6. Lack of interaction of p53as and p53 proteins mixed posttranslationally. Equal amounts of p53 and p53as translated in vitro were mixed and assayed for binding to $^{32}$P-labeled oligonucleotide by non-denaturing polyacrylamide gel electrophoresis (lane 1). 200 ng each of the indicated antibodies were added to the binding reaction.

Figure 7:
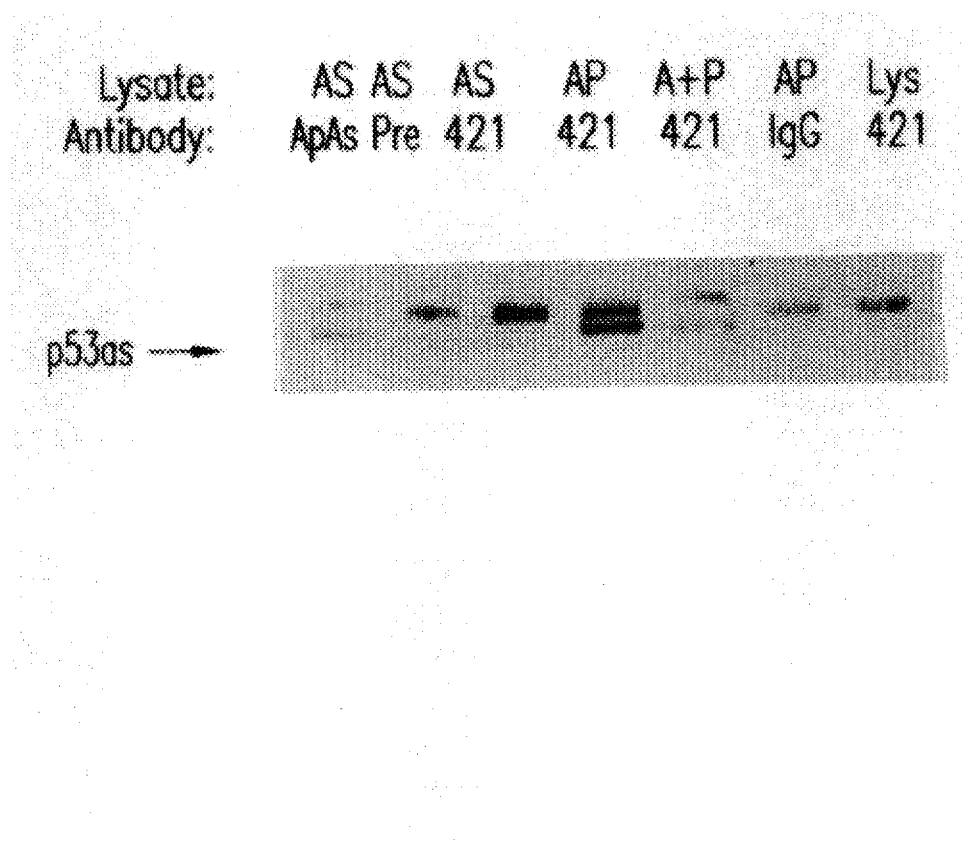

FIG. 7. Heteroligomers of p53 with p53as identified by immunoprecipitation followed by immunoblotting. In vitro translated proteins were p53as (AS), p53 (P), cotranslated p53 and p53as (AP) or a mixture of p53as plus p53 translated individually (A+P) and non-programmed reticulocyte lysate control (Lys). The translated proteins (15 μl each lysate, 30 μl for cotranslation) were immunoprecipitated with anti-p53 antibody PAb421 (421) rabbit antibody to p53as (ApAs), pre-immune (Pre) or IgG2a (IgG) controls. The immune complexes were fractionated on a 10% SDS-polyacrylamide minigel, transferred to a nitrocellulose membrane and incubated with horseradish peroxidase-conjugated ApAs for 1 hour. The p53as was visualized through chemiluminescence (ECL, Amersham, Arlington Heights, Ill.).

Figures 8A, 8B:
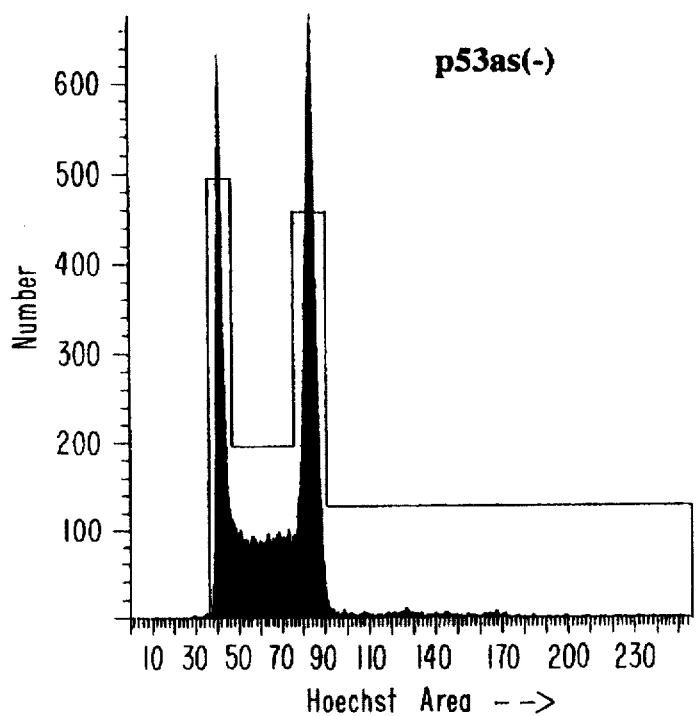

FIG. 8A is a table showing percent distribution of p53as reactivity at various stages of insect cell cycles after infection with baculovirus vector containing the full length p53as cDNA. Insect cells arrest in G2 phase of the cell cycle after infection with the baculovirus vector.

FIG. 8B is a graph showing p53as(−) distribution for insect cells.

Figure 8C:
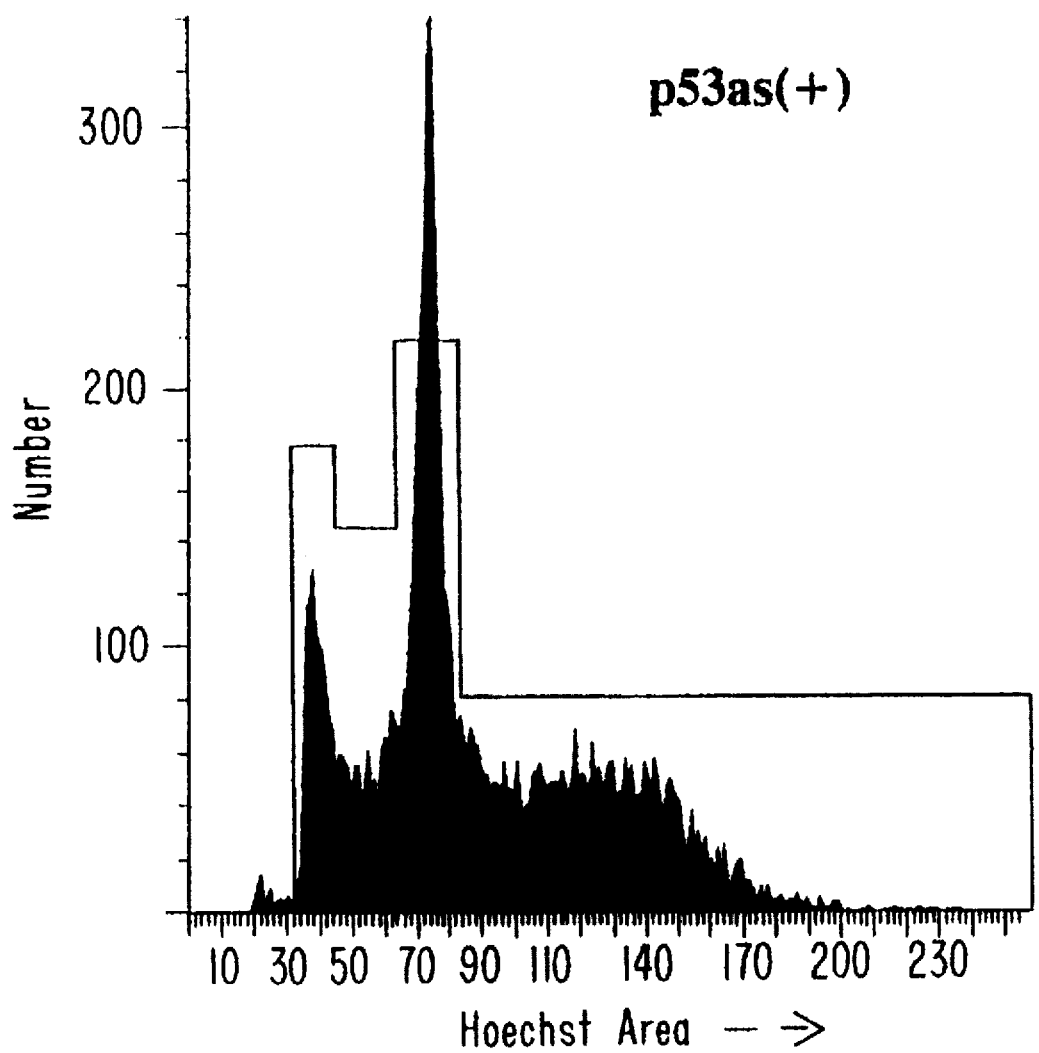

FIG. 8C is a graph showing p53as(+) distribution for insect cells.

Figures 9A, 9B:
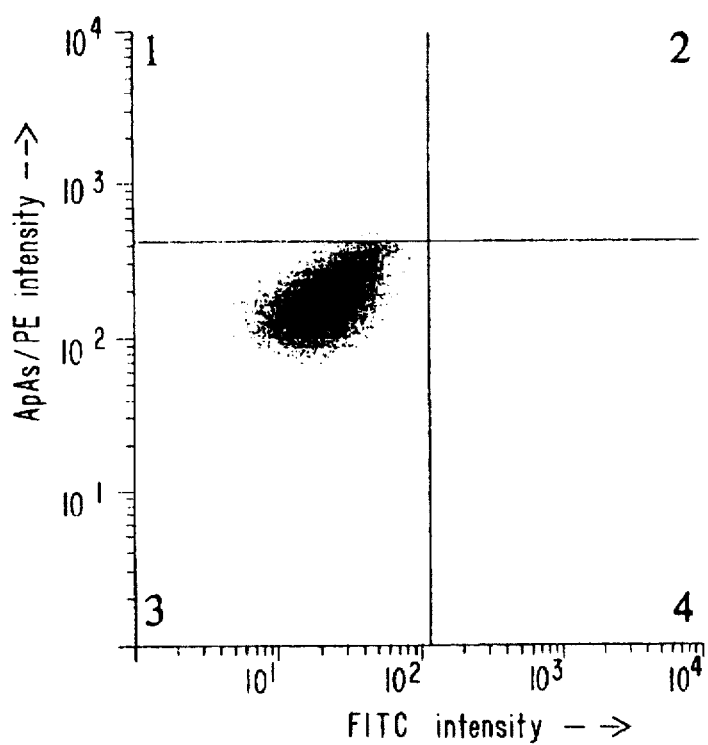

FIG. 9A is a table showing percent distribution of cells in various stages after being transfected with plasmid containing p53as cDNA and showing that transfected cells were preferentially distributed in the G2 phase of the cell cycle. The cells used are mouse squamous cell carcinoma cells which arrest in the G2 phase of the cell cycle after transfection with a plasmid construct containing p53as cDNA.

FIG. 9B shows distribution of ApAs/PE intensity vs. FITc intensity for mouse squamous cells.

Figure 9C:
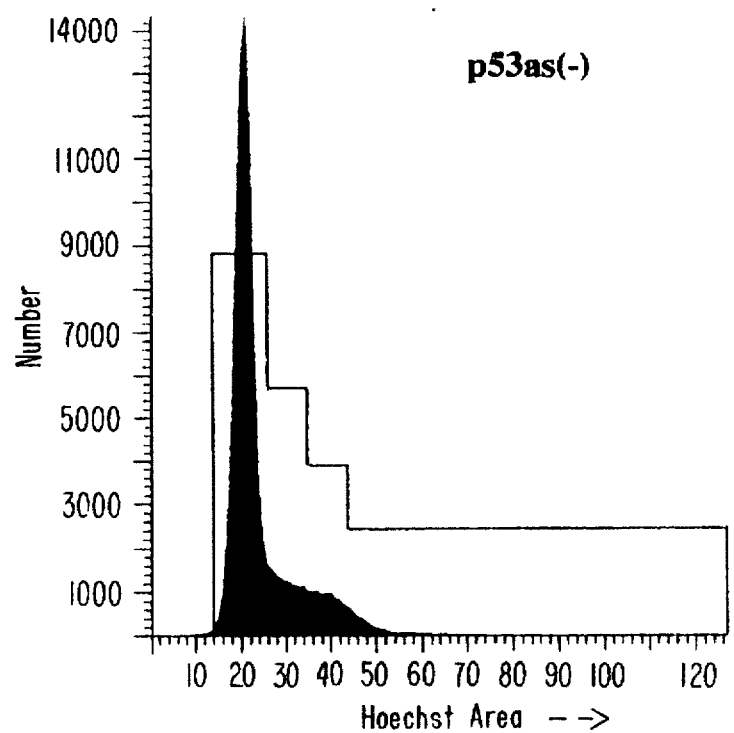

FIG. 9C is a graph showing p53as(−) for transfected mouse squamous cells.

Figure 9D:
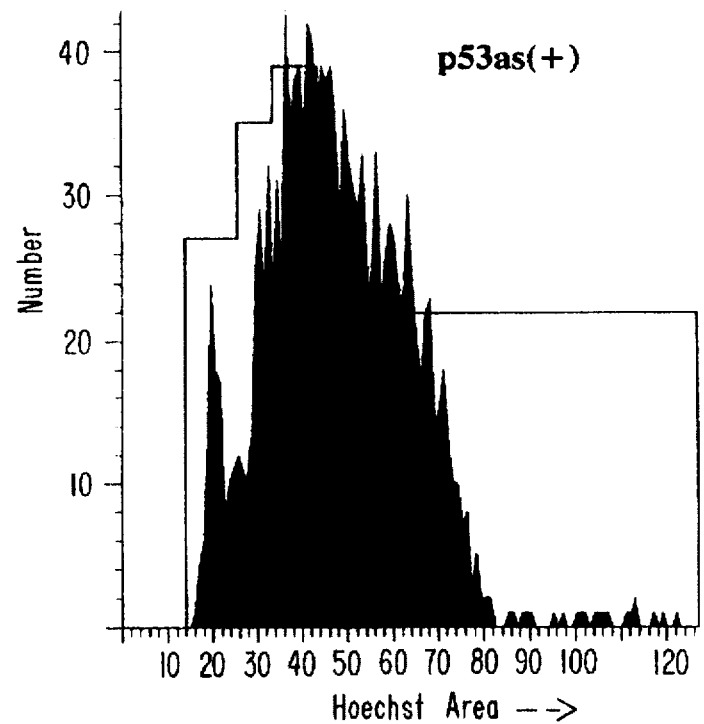

FIG. 9D is a graph showing p53as (+) for transfected mouse squamous cells.

FIGS. 10A, 10B and 10C show colony formation of Saos-2 cells transfected with CMV plasmids. FIG. 10A shows a control without a cDNA insect. FIG. 10B shows a p53as cDNA insect and FIG. 10C shows a p53 cDNA insect. Plasmid containing p53as containing a CMV promoter (which drives expression of p53as in the target mammalian cell) is introduced into human osteosarcoma cells which lack p53 which stops tumor cell growth and reduces the number and area of colonies present in the culture dishes. This assay is commonly used to show tumor suppressor activity of various genes and p53 used as a control shows similar activity, thus wild type p53as acts as a tumor suppressor. In contrast, a plasmid containing an alternatively spliced mutant p53 sequence had transforming activity (Eliyahu et al., Oncogene 3,313–321, 1988). Tumor suppressor activity was found in human cells as well as mouse cells. Human osteosarcoma cell line Saos-2 was transfected using lipofectin, BRL0 with 5 ng of the pCMV plasmids containing the p53 or p53as cDNA indicated and a neomycin resistance gene. Vector without the cDNA insert was used as a control. Forty-eight hours after transfection, cells were trypsinized, passaged at a 1:4 ratio and cultured in media containing 500 μg/ml G418 for 3 weeks. Colonies were fixed in methanol and stained with Giemsa and measured using an image analysis system (Spectra Services).

FIGS. 11A, 11B and 11C show gel filtration profiles of proteins translated in vitro. The in vitro translations were carried out as described in parent application Ser. No. 08/195,952. p53as (FIG. 11A), p53 (FIG. 11B) and cotranslated p53 and p53as (FIG. 11C) were fractionated by gel filtration (FPLC) on a Superose 6 column (Pharmacia) with column buffer (0.4M NaCl, 0.5% NP-20, 20 mM Tris-HCl, pH 7.2) at a flow rate of 0.4 ml/min. 0.4 ml eluant was collected in each fraction. The 35S-labeled proteins in each fraction were visualized by SDS-PAGE and autoradiography. Black arrows indicate the predicted positions of tetramers (4) and dimers (2) based on the positions of molecular weight standards, amylase (200 kd) and phosphorylase B (97 kd).

DETAILED DESCRIPTION OF THE INVENTION

Materials and Methods for the DNA Binding Studies

Plasmids for in vitro transcription and translation of p53as and p53 proteins.

Plasmids containing the cDNA sequence unique to p53as are included in this invention. One such plasmid is pBSp53as which contains full length alternatively spliced p53 cDNA. pBSp53as was constructed from p53 cDNA beginning at nt −111 of the (where 1 is the first ATG encoding methionine) and ending at nt 1539, cloned into the EcoRI and BamHI sites of pBluescript SK under the control of a T3 phage promoter. The N-terminal fragment of wt p53 was amplified by reverse transcriptase/polymerase chain reaction (RT-PCR) from a mouse epidermal cell RNA template and the C-terminal fragment of p53as was amplified by PCR from plasmid p6.4 (which contains an alternatively spliced p53 cDNA; Han and Kulesz-Martin, Nucl. Acids Res. 20: 1979–81, 1992) using primers which contained a StuI restriction site at the 5' end of the sense primer (AGTCAGGCCTTAGAGTTAAAGGATGCCCATGCTA-CAGA) (SEQ ID NO:2) and a BamHI site at the 5' end of the antisense primer. pBSp53 was made from pBSp53as by replacement of the StuI/BamHI C-terminal fragment of p53as cDNA with the StuI/BamHI segment of wild type p53 cDNA from plasmid pLSVNc51 (ref. Oren). In particular, cDNA for the N-terminus of p53 (nt −111 to 1090) was made using template RNA from 291 nontransformed epidermal cells by means of a reverse transcriptase reaction, amplified by PCR and cloned into the EcoRI and BamHI sites of pBluescript SK under the control of a T3 phage promoter to create plasmid pBSRS 13. The primers used for PCR were: sense, AGTCGAATTCATTGGGACCATCCTGGCT (SEQ ID NO:3), antisense, AGTCGGATCCTGGAGTGAGT-GAGCCCTGCTGTCT (SEQ ID NO: 4). These primers contained an EcoRI restriction site at the 5' end of the sense primer and a BamHI site at the 5' end of the antisense primer (denoted by underlining). The C-terminal p53 cDNA (nt1028 to 1539) was amplified by PCR from plasmid p6.4 (which contains an alternatively spliced p53 cDNA) using primers which contained a StuI restriction site at the 5' end of the sense primer (AGTCA-GGCCTTAGAGTTAAAGGATGCCCATGCTACAGA) (SEQ ID NO:2) and a BamHI site at the 5' end of the antisense primer (as in Hart and Kulesz-Martin, Nucl. Acids Res. 20: 1979–81, 1992). The StuI to BamHI segment of this PCR reaction product was then ligated to the StuI and BamHI sites of plasmid pBSRS13 to create plasmid pBSp53as, containing a full length alternatively spliced p53 cDNA. To construct pBSp53, the StuI and BamHI fragment from wt p53 cDNA was substituted for the StuI and BamHI fragment of the p53as cDNA in pBSp53as.

In Vitro Transcription and Translation

10 µg of plasmid pBSp53as or pBSp53 was linearized by BamHI and transcribed with 20 Units T3 RNA polymerase for immunoprecipitation studies and DNA binding studies. The in vitro translation was performed according to a standard protocol (Promega) by incubating 3 µg RNA with 35 µl of rabbit reticulocyte lysate. For immunoprecipitations, 4 µl (40 µCi) $^{35}$S-methionine was used for labeling of proteins. For co-translation of p53as and p53, an equal amount of each RNA was incubated with rabbit reticulocyte lysate (Promega).

Immunoprecipitation was performed by incubating 5 µl $^{35}$S-labeled protein with 1 µg PAb421, ApAs or PAb246 at 4° C. overnight. Protein A-Sepharose 4B was then added with gentle mixing at 4° C. for 2 hr. After centrifugation, the pellets were washed three times with Net-gel buffer. The pellets were suspended in 2× sample buffer containing 100 mM DTT and separated by electrophoresis in a 7.5% SDS-polyacrylamide minigel. The gel was enhanced, dried and exposed overnight to Kodak X fill. Two lysate reactions are shown, p53 or p53as RNA—see labels at top. Antibodies used to immunoprecipitate protein from each lysate reaction are indicated.

For the DNA binding assay, 3 ug of sense RNA for p53 or p53as was added to 35 µl reticulocyte lysate and adjusted to a total volume of 50 µl for translation in vitro. For cotranslations, half the amount of each RNA was used. An aliquot of 5 µl of translation mixture (or 2.5 µl each lysate for the mixing experiments) was incubated with 2 µg poly [d(I-C)] and 30,000 cpm (approximately 1 ng) of $^{32}$P-end-labeled DNA probe in 20 µl DNA binding buffer (0.1% Triton x-100, 4% glycerol, 1 mM EDTA, 5mMDTT, 20 mM Tris-HCl, pH 7.2, 80 mM NaCl) at 4° C. for 20 min. Where indicated, 200 ng of antibody was included in the reaction. Reaction products were separated on a 4% neutral polyacrylamide gel in 0.5× TBE buffer. The gel was dried and labeled binding complexes were visualized by radioantography.

Results, p53as Protein Binding to DNA

As presented in the original patent application, we suggested that p53as protein would be active for binding to DNA. DNA binding of the major p53 form is considered essential for its function as a cell cycle control gene. DNA binding is required for its activity as a transcription factor which controls the expression of other genes. The interaction of p53 with other proteins is of intense interest in the scientific community because such p53-associated factors may control the activity of p53 by affecting its binding to DNA. The data presented herein demonstrates that p53as protein binds to DNA, and that p53as and p53 protein associate with each other, suggesting that p53as is a newly discovered p53-associated protein.

The p53as protein has lost basic amino acids but has retained acidic amino acids important for oligomerization. The sequence-specific DNA binding activity of p53as protein translated in vitro, separately, or cotranslated with p53 protein, was studied in an attempt to answer the following questions: 1) does p53as protein, like the major p53 form, have sequence-specific DNA binding activity? and 2) does p53as protein interact with p53, modulating its ability to form a complex with DNA?

To answer these questions, specific antibodies to p53 and to p53as proteins were used (Table 1). The specificity of the antibodies was tested by competition with the p53as peptide as reported in the original patent application. Further evidence for specificity of the p53as antibody is reactivity of anti-p53as with p53as protein translated in vitro but not with the major p53 protein. The commercially available antibody PAb421 which is specific for an epitope lacking in p53as reacted with p53 protein translated in vitro but not with p53as protein (FIG. 2.) This ensured that these antibodies would not cross react with the two proteins in the DNA binding assays. Therefore, the ability of the anti-p53as antibody to shift a complex between in vitro translated p53as protein or p53+p53as cotranslated protein clearly indicates that p53as protein must be present in the protein/DNA complex.

In order to answer the first question above, electrophoretic mobility shift assays were performed using a $^{32}$P-labeled double-stranded oligonucleotide probe corresponding to the p53 binding sequence shown in Table 2. As shown in FIG. 2, p53as protein translated in vitro gave a strong signal representing a shift from free probe (dark signal at bottom of figure) to a higher molecular weight complex composed of protein and the labeled DNA probe. The p53as protein bound specifically to the p53 binding sequence, as shown by loss of the band with unlabeled competing DNA probe (wt) being included in the reaction but not with unlabeled oligonucleotide corresponding to the mutated p53 binding sequence (mut). (Note that the first weak band above the free probe is nonspecific). The identity of the shifted band as a complex containing p53as is shown by supershifting of the p53as/DNA complex by anti-p53as antibody (ApAs) but not by preimmune serum (Pre) or anti-p53 antibody PAb421. The supershift of p53as protein by ApAs resulted in two higher molecular weight bands. Further verification of the ApAs reactive protein as a product of the p53 gene is provided in FIG. 3 by loss of the signal in the presence of anti-p53 antibodies PAb246 and CMS, which react with both p53 and p53as proteins.

In contrast, the binding of the major p53 form to specific DNA binding sequences is inefficient and requires activation (Hupp, et al., 1992). FIG. 4 demonstrates that the major p53 form translated in vitro is not active for DNA binding but required activation by PAb421. Activated p53 bound to DNA and resulted in a supershift of a single high molecular weight complex.

Because p53 has been reported to self-associate to form oligomers, for example dimers and tetramers (Stenger et al., 1992), and because p53as has retained acidic amino acids but not basic amino acids important for dimer and tetramer formation, the DNA binding of p53 and p53as proteins, translated together or mixed after separate translation, was examined. As shown in FIG. 5, cotranslated p53 reduced the signal for DNA binding compared to p53as alone. This appears to be due to a direct association of p53 and p53as proteins because PAb421 antibody now resulted in a supershift of two bands rather than the one obtained with p53 alone.

In contrast to cotranslation of p53 and p53as proteins, mixture of lysates containing each protein translated individually did not show inactivation of p53as by p53 protein for DNA binding, and PAb421 supershifted only one band, suggesting that p53 and p53as must be translated together for association to occur (FIG. 6). This is consistent with the report that oligomerization between human p53 and mouse p53 occurs when they are cotranslated, but not when mixed (Milner and Medcalf, 1991).

In order to directly test the ability of p53 protein to form a complex with p53as protein, immunoprecipitation of cotranslated proteins was done using PAb421 and the immunoprecipitated proteins were resolved by denaturing gel electrophoresis, blotted and exposed to ApAs antibody. Proteins in complex with the protein immunoprecipitated by the specific antibody will also precipitate. Proteins not in complex will not. The lower band in the immunoblot shown in FIG. 7 is the p53as band. These results indicated that cotranslated p53as and p53 proteins contain complexes of p53 and p53as immunoprecipitable by PAb421 and blotted by ApAs. A much weaker signal is generated in mixtures of p53 and p53as proteins translated individually, indicating that for stable complexes to form the proteins must be cotranslated.

Summary and Interpretations of DNA Binding Studies p53as protein exhibited the antibody binding properties of wild type p53 protein, PAb246+, PAb240−, but lacked the C-terminal epitope reactive with PAb421. p53as protein translated in vitro was activated for binding to a p53 DNA binding sequence. The major p53 protein, in contrast, required activation for DNA binding (by monoclonal antibody PAb421). There appears to be a direct interaction between p53as and p53 proteins which influenced the composition of the DNA binding complex and the magnitude of DNA binding. Because cotranslated p53 protein inactivated p53as protein for DNA binding, and because two bands were super-shifted by PAb421 in lysates containing p53as and p53 cotranslated proteins, compared to one band in lysate containing p53 alone, these results could be explained by binding to DNA of p53as and p53/p53as heterooligomers, in addition to the binding of p53.

The significance of these findings is that they are consistent with a functional role for p53as protein in cells, which may, at least in part, be distinct from the function(s) of the major p53 protein form. Considering that vectors and plasmids containing the p53 gene are being tested for applications in gene therapy, and considering the results herein that p53as is active for binding to a p53 binding sequence and that p53as interacts with p53, resulting in altered DNA binding, plasmids and vectors for the expression of mouse and human p53as in cells and for uses in gene therapy in humans are claimed herein.

Cellular Function of p53 as

In the original patent application the association of p53as antigen activity with cells distributed primarily in the G2 phase of the cell cycle was presented. This was an important clue that p53as might have a distinct function compared to p53 protein. In order to examine whether p53 as protein might have a direct role in cell cycle arrest, a DNA sequence containing the entire coding sequence of p53as was constructed. This sequence is different from the p53 coding sequence, as presented in the original patent application, and is different from previously reported DNA constructs. Constructs containing the p53as cDNA were expressed in insect cells and in mammalian cells and effects on the cell cycle distribution of cells were evaluated.

Materials and Methods for p53as Expression Studies

Insect cells

Methods were per manufacturers instructions (Invitrogen) and materials and included linear AcMNPV DNA and transfer vector (e.g. pVL 1392, pVL 1393) and insect cell line *S. frugiperda* Sf9, propagated at 27° C. in Grace's supplemented insect medium containing 10% fetal bovine serum (GIBCO) and 10 µg/ml gentamycin sulfate. pVL1393BGB53 baculovirus vector containing wt p53 cDNA was constructed by inserting the BglII/BamHI fragment of pLSVNc51 (including the entire wt p53 cDNA) into the pVL 1393 vector. pVL1393Asp baculovirus vector (containing p53as cDNA) was constructed by replacement of the StuI/BamHI C-terminal fragment of p53as cDNA (Han and Kulesz-Martin, Nucl. Acids Res. 1992) with the BamHI/StuI fragment of the pVL1393BGB53 vector (see above). To purify recombinant viruses, Sf9 cells were cotransfected with linear AcMNPV DNA and the transfer vector containing p53as and grown for 3 days. Recombinant viruses were identified by plaque assays or serial dilutions. Alternatively, p53 and p53as baculovirus contructions will be cotransfected with linearized (PharMingen) virus DNA which allows propagation of only recombinant virus. Virus stocks which resulted in p53 as expression in insect cells (assayed by immunoblotting using anti-p53as antibody) were expanded and used to infect insect cells for the flow cytometry studies.

Baculovirus pVL1393Asp stock was added to insect cell cultures at 3×10$^6$ cells/60 mm dish. After several (2 to 4) days, cells were harvested by trypsinization and stained with anti-p53as antibody and analyzed by flow cytometry as detailed in the original patent application.

Mammalian Cells

Plasmids

Plasmids for expression of p53as in mammalian cells were constructed. An example is given of the full length p53as cDNA under the control of a metallothionein promoter. However, other promoters which may increase or decrease expression in given cell types, such as the cytomegalovirus promoter, will be used as appropriate. pmMTBGB containing the full length wild type p53 cDNA beginning at −67 nt (where nucleotide 1 is the first nucleotide of the first ATG codon) was constructed by replacement of the BglII/BamHI fragments of plasmid pmMTval53cG (from M. Oren) with the BglII/BamHI fragment of plasmid pLSVNc51 noted above. The pmMTAsp plasmid was constructed by firstly, replacement of the XhoI/BamHI fragment of pmMTBGB with the XhoI/BamHI fragment of pVL1393Asp and secondly, introduction of a BamHI fragment from plasmid BCMGNeo (Karasuyama and Melchers, 1988) containing the splicing signals and polyA tail of the rabbit B-globin gene.

Transfection

Mouse squamous cell carcinoma cells (291.05RAT) were plated in culture medium at 2 to 3×10$^6$ per 60 mm dish and transfected with plasmid pmMTAsp when 40 to 60% confluent using Lipofectin (GIBCO BRL). 10 µg of plasmid diluted in 100 µl ddH$_2$O was mixed with 30 µl Lipofectin adjusted to 1 ml with serum-free culture medium, incubated with the cell cultures for 20 hr, then removed and replaced with culture medium with serum. 24 hr later CdCl$_2$ was added to the cells to stimulate transcription of p53as mRNA from the plasmid DNA and enhance the expression of p53as protein. Two days later, cells were harvested by trypsinization, stained with anti-p53as antibody and analyzed by flow cytometry as described in the original patent application.

Results of p53 as Expression Studies

Insect cells

Approximately 12% of insect cells infected with the baculovirus vector containing p53as expressed p53as antigen activity compared to 0% of insect cell controls lacking exogenous p53as cDNA. Insect cells expressing p53as protein were primarily in the G2 phase of the cell cycle or in a "tail" representing cells containing >G2 DNA content (FIG. 8). Control insect cells were primarily distributed in the G1 phase of the cell cycle.

The significance of these studies is likely to be relevant to cell cycle control in mammalian cells. Other cells which do not have the p53 gene have proven very useful for studies of the role of p53 protein in cell cycle control. For example, while yeast does not contain the p53 gene, studies of p53 in yeast have been done to take advantage of the knowledge of cell cycle checkpoints and cell cycle regulatory proteins gained using the yeast model. The studies in yeast have been very informative, since p53 protein behaves in yeast cells in a manner consistent with its cell cycle role in mammalian cells (Nigro et al., 1992; Bischoff et al., 1992).

Mammalian Cells

As in the case of the insect cells, mouse carcinoma cells transfected with the plasmid containing p53as cDNA were preferentially distributed in the G2 phase of the cell cycle or in a "tail" representing cells containing >G2 DNA content (FIG. 9).

Summary and Interpretations of p53as Expression Studies

These data indicate that expression of p53as by introduction into cells leads to accumulation of cells in the G2 phase of the cell cycle or exit from the cycle to a state in which DNA content is greater than G2 cells. A likely explanation for this is an arrest of cells within G2 and failure to undergo mitosis and proceed to the G1 or G0 phase of the cycle.

Significance of p53as Expression Studies

These data are consistent with a checkpoint function of p53as at the G2/M phase of the cell cycle. Activity of p53as expression in causing cells to exit from the cell cycle would have useful applications in gene therapy of proliferative disorders such as cancer or psoriasis.

Because human and mouse p53 proteins form complexes in cells, the construct containing mouse p53as cDNA is claimed for the purposes of gene expression in mammalian cells and nonmammalian cells for research purposes, including human cells, and for gene therapy in humans. In addition, a purified plasmid construct containing the human p53as homologue of mouse p53as, defined by insertion of human intron 10 sequences into a sequence containing wt p53 DNA (as defined in original patent application Ser. No. 08/100,486) is claimed for research purposes in mammalian and nonmammalian cells, and for gene therapy in humans.

Table 1. shows reactivities of antibodies against p53 proteins. Mouse p53 has 390 amino acids; human p53 393 amino acids. All antibodies are mouse monoclonals commercially available from Oncogene Science, Cambridge Mass., except ApAs rabbit polyclonal specific for p53as protein which was made in Dr. Kulesz-Martin's laboratory, RPCI. Sources: Oncogene Science Catalogue, p. 8, 1992; Vajtesek et al., J. of Immunolog. Methods 151:237–244, 1992, [a]Wade-Evans, A. and Jenkins, J. R. EMBO J., 4:699–706, 1985, [b]Gannon, EMBO, 9:1595–1602, 1990, [c]Stephen, C. W. and Lane, D. P., J. Mol. Biol., 5:577–583, 1992 and [d]Kulesz-Martin et al., Mol. Cell. Biol., in press, March 1994.

Table 2. shows p53 DNA Binding Sequences used for assay of p53as protein binding activity.

Table 3 shows Activation of 50-2 Muscle Creatinin Kinase Reporter Plasmid by p53as in Mouse Cells. Spontaneously arising immortalized murine BALB/c embryo fibroblast (10) 1 is a p53 negative cell line which was transfected with 2 µg pSV-β-gal plasmid (Promegal), 3 µg 50-2 plasmid (Dr. Levine) which contains 2 copies of a 50 bp sequence corresponding to p53 binding site in muscle creatinine kinase promoter-enhancer upstream of a basic CAT reporter plasmid, and 5 µg pCMVp53as, pCMVp53r or pCMV vector control. Transfection was done using the calcium phosphate method. The cells were harvested 48 hours post-transfection and lysed by three freeze-thaw cycles. The supernatant was assayed for CAT activity using diffusion.

Table 4 shows activation of PG13CAT Plasmid by p53as in Human Saos-2 Cells. The human ostoesarcoma Saos-2 cells were transfected with 3 µg of PG13CAT plasmid, which contains 13 repeats of p53-binding site upstream of a CAT reporter gene with a basal promoter and 5 µg pCMVp53as plasmid, pCMVp53r or pCMV vector control plasmid. Transfection was done using the calcium phosphate method and the total transfected DNA per plate was adjusted to 10 µg with herring sperm DNA. The cells were harvested 48 hours post-transfection and lysed by three freeze-thaw cycles. Cell debris was removed by centrifugation and the supernatant was assayed for CAT activity using the diffusion method.

Tables 3 and 4 demonstrate that p53as has transcriptional activity. Plasmids containing p53as, or p53 as a control, were introduced into mouse or human cells along with a plasmid containing a p53 binding site upstream of a reporter gene. The reporter was activated by p53as, with p53 as a positive control, but not by the vector without p53as. By comparison, the background activity of the reporter plasmid alone was low. The reporter sequences 50-2 and PC13 are a promoter-enhancer sequence (Zambetti et al., Genes Dev. 6, 1143–1152, 1992) and a consensus p53 binding sequence (Kern et al., Science 256, 827–830, 1992). p53 as was active on mouse (50-2) or human (PC13) p53 binding sequences, and in both mouse and human cells.

Table 5 shows Activation of the WAF-1 Promoter by p53as in Mouse Cells. Cells of mouse fibroblast line Dr. Levine (10)1 were transfected with 2 µg pSVCAT (Promega). 3 µg WWP-1 (Dr. B. Vogelstein) which contains the WAF-1 promoter upstream of a luciferase reporter gene and 5 µg of pCMVp53as, pCMVp53r or pCMV vector control were transfected using the calcium phosphate method. 48 hours later the cells were harvested and lysed in reporter lysis buffer (promega). The supernatant was assayed for luciferase activity using a LB9501 luminometer. Luciferase activity was standardized to CAT activity.

Table 5 demonstrates that p53as activates transcription from an endogenous promoter region of a growth inhibitory gene, WAF-1, cipl, sdi, p21 (El-Deiry et al., Cell 75, 817–825, 1993; Gu et al., Nature 366, 707–710, 1993; Harper et al., Cell 75, 805–816, 1993; Xiong et al.; Nature 366, 701–704, 1993; and Serranto et al, Nature 366, 704–705, 1993 ) recently reported to be a target gene of p53 in cells and a cell cycle control gene. The activity of p53as for the WAF-1 promoter is therefore strong evidence that p53as has transcriptional activity in vivo for genes functional in cell cycle control.

The similarities between p53 and p53as are that both act as tumor suppressors, both activate transcription and both forth tetramers which bind specifically to DNA. The differences between p53as and p53 are that the p53 protein is activated under conditions in which p53 requires activation, p53as is associated with a different cell cycle stage compared to p53 and therefore have different functions or different regulation of activity. These differences suggest that plasmids containing p53as and the antibodies for p53as have utility as described herein and that utility may be different in some respects from that of plasmids containing p53.

For example, minor cells which express different ratios of p53as and p53, as detected at the RNA level, or at the protein level by anti-p53as antibodies may have different characteristics or different sensitivity to anti-cancer treatments. Different characteristics identifiable by reactivity with p53as antibodies could aid in the diagnosis of cancer, proguosis for individual patients with tumors and decisions about treatment based on the competency of the p53as functions in the tumor. Antibodies to p53 are being used clinically in diagnosis of human cancers because expression of p53 at detectable levels has been found to correlate with cancer prognosis for a variety of human tumor types. It is known that tumors with defective p53 genes (more than 50% of all human cancers) fail to control cell cycle progesssion normally. Since p53 and p53as have different cell cycle associations, tumor typing using specific p53as antibodies and specific anti-p53 antibodies may increase the value of typing individual tumors according to their expression of tumor suppressor gene products such as p53. Such tumor typing may provide useful information in the diagnosis, prognosis, and treatment strategy of individual patient cancers.

Gene therapy strategies are being devised for introduction of anti-cancer genes into tumors for treatment of human cancers. Plasmids or vectors containing the p53as sequence of mouse or human may be useful for gene therapy approaches, based on the ability of plasmids containing mouse p53as to act as a minor suppressor and to activate transcription of p53 target genes.

TABLE 1

Reactivites of Antibodies Agains p53 Proteins

| Ab | Species | wt conform | wt denatured | mutated | p53 | p53as | epitope | IP | WIB | cell staining | frozen sections | paraffin sections |
|---|---|---|---|---|---|---|---|---|---|---|---|---|
| PAb421* | mu/hu | + | + | + | + | − | 370–378 | + | +/− | + | + | − |
| PAb246* | mu | + | − | − | + | + | 88–109 | + | − | + | + | nt |

TABLE 1-continued

Reactivites of Antibodies Agains p53 Proteins

| Ab | Species | wt conform | wt denatured | mutated | p53 | p53as | epitope | IP | WIB | cell staining | frozen sections | paraffin sections |
|---|---|---|---|---|---|---|---|---|---|---|---|---|
| PAb240[b,c] | mu/hu | – | + | + | + | (–) | 210–214 | + | + | + | + | – |
| ApAs[d] | mu | + | + | nt | – | + | (364–381) | + | + | + | nt | nt |

Mouse p53 has 390 amino acids; human p53 393 amino acids. All antibodies are mouse monoclonals commercially available from Oncogene Science, Cambridge MA, except ApAs rabbit polyclonal specific for p53as protein which was made in Dr. Kulesz-Martin's laboratory, RPCI. Sources: Oncogene Science Catalogue, p. 8, 1992; Vajtsesek et al., J. of Immunolog. Methods 151:237–244, 1992, [a]Wade-Evans, A. and Jenkins, J. R. EMBO J., 4:699–706, 1985, [b]Gannon, EMBO, 9:1595–1602, 1990, [c]Stephen, C. W. and Lane, D. P., J. Mol. Biol. 5:577–583, 1992 and [d]Kulesz-Martin et al., Mol. Cell. Biol., in press, Man 1994.

TABLE 2

Known p53 DNA Binding Sequences.

1. AGGCWWGCCT (SEQ ID NO: 9)
p53 binding sequence
AGGCATGCCT (SEQ ID NO: 5) AGGCATGCCT (SEQ ID NO: 5)
mutated sequence used for negative control (small letters indicate nucleotide substitutions)
AGGaATtCCT (SEQ ID NO: 6)/AGGaATtCCT (SEQ ID NO: 6)
Ref.: El-Deiry, W. S., Kern, S. E., Pietenpol, J. A., Kinzler, K. W. and Vogelstein, B. (1992) Nature 358, 83–86.
2. TGGCAAGCCTATGACATGGCCGGGGCCTGCCTCTCTCTGCCTCTGACCCT (SEQ ID NO: 7)
Ref.: Zambetti, G., Bargonetti, J., Walker, K., Prives, C., and Levine, A. (1992) Gene & Development 6, 1143–1152
3. GACACTGGTCACACTTGGCTGCTTAGGAAT (SEQ ID NO: 8)
Ref.: Foord, O., Navot, N., and Rotter, V. (1993) Mol. Cell. Biol. 13(3), 1378–1384

TABLE 3

Activation of 50-2 Muscle Creatinine Kinase Reporter Plasmid by p53as in Mouse Cells

| | CAT Activity (cpm) | Fold of activation |
|---|---|---|
| Vector | 1,457 | 1 |
| p53as | 37,185 | 26 |
| p53 | 39,855 | 27 |

TABLE 4

Activation of $PG_{13}CAT$ Plasmid by p53as in Human Saos-2 Cells

| | CAT Activity (cpm) | Fold of activation |
|---|---|---|
| Vector | 2,539 | 1 |
| p53as | 23,319 | 9 |
| p53 | 35,190 | 14 |

TABLE 5

Activation of the WAF-1 Promoter by p53as in Mouse Cells

| | Luciferase Activity | Fold of activation |
|---|---|---|
| Vector | 481 | 1 |
| p53as | 6,855 | 14 |
| p53 | 7,010 | 15 |

What is claimed is:

1. A method for determining the presence and concentration of p53as in a cell sample comprising:
   a) reacting the cell sample with an antibody which specifically binds to mammalian p53as protein and does not bind to normal p53 from the same species wherein said antibody binds to an epitope present in a peptide unique to p53as, said peptide occurring within the final 50 carboxyl terminal amino acids of p53as;
   b) determining the presence and concentration of p53as bound with said antibody; and
   c) comparing the determined concentration of p53as in the cell sample with p53as concentrations in normal cell products.

2. The method of claim 1 wherein the normal p53 protein is a mouse p53 protein.

3. The method of claim 1 wherein the normal p53 protein is a human p53 protein.

4. The method of claim 1 wherein the antibody is a polyclonal antibody.

5. The method of claim 1 wherein the antibody is a monoclonal antibody.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 21
        ( B ) TYPE: Amino Acid
        ( C ) STRANDEDNESS: Unknown
        ( D ) TOPOLOGY: Unknown ( i i ) MOLECULE TYPE: Peptide ( i i i ) HYPOTHETICAL: No ( i v ) ANTI-SENSE: No ( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT: 17
        ( B ) MAP POSITION: intron 10
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO: 1:

Ser Leu Arg Pro Phe Lys Ala Leu Val Arg Glu Lys Gly His Arg Pro
            5                    10                15

Ser Ser His Ser Cys
      20

( 2 ) INFORMATION FOR SEQ ID NO: 2:

( i ) SEQUENCE CHARACTERISTICS:
        ( A ) LENGTH: 38
        ( B ) TYPE: Nucleic Acid
        ( C ) STRANDEDNESS: Unknown
        ( D ) TOPOLOGY: Unknown (i i) MOLECULE TYPE:

(i i i) HYPOTHETICAL: No (i v) ANTI-SENSE: No (v) FRAGMENT TYPE:

(v i) ORIGINAL SOURCE:
    (A) ORGANISM: Murine
    (B) STRAIN: Balb/c
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE:
    (A) LIBRARY:
    (B) CLONE:

(v i i i) POSITION IN GENOME:
    (A) CHROMOSOME/SEGMENT:
    (B) MAP POSITION:
    (C) UNITS:

(i x) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS: K. Han, M. Kulesz-Martin
    (B) TITLE: ALTERNATIVELY SPLICED p53 RNA IN
          TRANSFORMED AND NORMAL CELLS OF
          DIFFERENT TISSUE TYPES
    (C) JOURNAL: Nuc. Acids Res.
    (D) VOLUME: 20
    (E) ISSUE: 8
    (F) PAGES: 1979-81
    (G) DATE: 1992
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO: 2:

```
AGTCAGGCCT TAGAGTTAAA GGATGCCCAT GCTACAGA                    38
```

(2) INFORMATION FOR SEQ ID NO: 3:

(i) SEQUENCE CHARACTERISTICS:
        (A) LENGTH: 28
        (B) TYPE: Nucleic Acid
        (C) STRANDEDNESS: Unknown
        (D) TOPOLOGY: Unknown (i i) MOLECULE TYPE:

(i i i) HYPOTHETICAL: No (i v) ANTI-SENSE: No (v) FRAGMENT TYPE:

(v i) ORIGINAL SOURCE:
        (A) ORGANISM: Murine
        (B) STRAIN: Balb/c
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 3:

AGTCGAATTC ATTGGGACCA TCCTGGCT        28

(2) INFORMATION FOR SEQ ID NO: 4:

(i) SEQUENCE CHARACTERISTICS:
        (A) LENGTH: 34
        (B) TYPE: Nucleic Acid
        (C) STRANDEDNESS: Unknown
        (D) TOPOLOGY: Unknown (ii) MOLECULE TYPE:

(iii) HYPOTHETICAL: No (iv) ANTI-SENSE: No (v) FRAGMENT TYPE:

(vi) ORIGINAL SOURCE:
        (A) ORGANISM: Murine
        (B) STRAIN: Balb/c
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:

(D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 4:

AGTCGGATCC TGGAGTGAGT GAGCCCTGCT GTCT            34

(2) INFORMATION FOR SEQ ID NO: 5:

(i) SEQUENCE CHARACTERISTICS:
        (A) LENGTH: 10
        (B) TYPE: Nucleic Acid
        (C) STRANDEDNESS: Unknown
        (D) TOPOLOGY: Unknown (ii) MOLECULE TYPE:

(iii) HYPOTHETICAL: No (iv) ANTI-SENSE: No (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS: El-Deiry et al.
        (B) TITLE: n/a
        (C) JOURNAL: Nature
        (D) VOLUME: 358
        (E) ISSUE: n/a
        (F) PAGES: 83-86
        (G) DATE: 1992
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 5:

AGGCATGCCT            10

(2) INFORMATION FOR SEQ ID NO: 6:

(i) SEQUENCE CHARACTERISTICS:
        (A) LENGTH: 10
        (B) TYPE: Nucleic Acid
        (C) STRANDEDNESS: Unknown (D) TOPOLOGY: Unknown (ii) MOLECULE TYPE:

(iii) HYPOTHETICAL: No (iv) ANTI-SENSE: No (v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS: El - Deiry et al.
                (B) TITLE: n/a
                (C) JOURNAL: Nature
                (D) VOLUME: 358
                (E) ISSUE: n/a
                (F) PAGES: 83-86
                (G) DATE: 1992
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO: 6:

AGGAATTCCT                                                      10

(2) INFORMATION FOR SEQ ID NO: 7:

(i) SEQUENCE CHARACTERISTICS:
                (A) LENGTH: 50
                (B) TYPE: Nucleic Acid
                (C) STRANDEDNESS: Unknown
                (D) TOPOLOGY: Unknown (ii) MOLECULE TYPE:

(iii) HYPOTHETICAL: No (iv) ANTI-SENSE: No (v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS: Zambetti et al.
    (B) TITLE: WILD-TYPE p53 MEDIATES POSITIVE REGULATION OF GENE EXPRESSION THROUGH A SPECIFIC DNA SEQUENCE ELEMENT
    (C) JOURNAL: Genes & Development
    (D) VOLUME: 6
    (E) ISSUE: n/a
    (F) PAGES: 1143-52
    (G) DATE: 1992
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO: 7:

```
TGGCAAGCCT ATGACATGGC CGGGGCCTGC CTCTCTCTGC CTCTGACCCT          50
```

(2) INFORMATION FOR SEQ ID NO: 8:

(i) SEQUENCE CHARACTERISTICS:
        (A) LENGTH: 30
        (B) TYPE: Nucleic Acid
        (C) STRANDEDNESS: Unknown
        (D) TOPOLOGY: Unknown (ii) MOLECULE TYPE:

(iii) HYPOTHETICAL: No (iv) ANTI-SENSE: No (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:

(A) AUTHORS: Foord et al.
            (B) TITLE: ISOLATION AND CHARACTERIZATION OF
                DNA SEQUENCES THAT ARE SPECIFICALLY
                BOUND BY WILD-TYPE p53 PROTEIN
            (C) JOURNAL: Mol. Cell. Biol.
            (D) VOLUME: 13
            (E) ISSUE: 3
            (F) PAGES: 1378-84
            (G) DATE: 1993
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 8:

GACACTGGTC ACACTTGGCT GCTTAGGAAT                    30

(2) INFORMATION FOR SEQ ID NO: 9:

(i) SEQUENCE CHARACTERISTICS:
                (A) LENGTH: 10
                (B) TYPE: Nucleic Acid
                (C) STRANDEDNESS: Unknown
                (D) TOPOLOGY: Unknown (ii) MOLECULE TYPE:

(iii) HYPOTHETICAL: No (iv) ANTI-SENSE: No (v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS: El - Diery et al.
                (B) TITLE: DEFINITION OF A CONCENCUS BINDING
                    SITE FOR p53
                (C) JOURNAL: Nature Genetics
                (D) VOLUME: 1
                (E) ISSUE:
                (F) PAGES: 45-49
                (G) DATE: April, 1992
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO: 9:

AGGCWWGCCT                                         10